United States Patent [19]

Opitz et al.

[11] Patent Number: 5,059,396
[45] Date of Patent: Oct. 22, 1991

[54] ARRANGEMENT FOR OPTICAL MEASURING OF CONCENTRATION OF SUBSTANCES

[75] Inventors: Norbert Opitz, Schwerte; Dietrich W. Lübbers, Dortmund; Bernhard Schrader, Essen, all of Fed. Rep. of Germany

[73] Assignee: Max Planck Gesellschaft zur Förderung der Wissenschaften E.V., Göttingen, Fed. Rep. of Germany

[21] Appl. No.: 249,586

[22] Filed: Sep. 26, 1988

Related U.S. Application Data

[63] Continuation-in-part of Ser. No. 889,810, Jul. 24, 1986, abandoned, which is a continuation of Ser. No. 679,018, Dec. 6, 1984, abandoned.

[30] Foreign Application Priority Data

Dec. 6, 1983 [DE] Fed. Rep. of Germany ....... 3344019

[51] Int. Cl.$^5$ .............................................. G01N 21/00
[52] U.S. Cl. .................................... 422/82.11; 422/83; 422/91; 359/123; 359/141
[58] Field of Search ................... 422/82.11, 56, 57, 58, 422/68, 83, 86, 87, 91; 436/95, 113, 163, 169, 170; 128/633, 634; 250/338, 340, 343; 356/317, 318, 445; 350/96.29, 96.32, 96.33, 96.34

[56] References Cited

U.S. PATENT DOCUMENTS

| | | | |
|---|---|---|---|
| 3,754,867 | 8/1973 | Guenther | 436/163 |
| 3,825,342 | 7/1974 | Lübbers et al. | 356/41 |
| 4,001,595 | 1/1977 | Reisman | 356/386 |
| 4,003,707 | 1/1977 | Lübbers et al. | 356/39 |
| 4,040,691 | 8/1977 | David et al. | 312/31 |
| 4,071,298 | 1/1978 | Falconer | 356/338 |
| 4,106,909 | 8/1978 | David et al. | 23/232 R |
| 4,169,676 | 10/1979 | Kaiser | 356/39 |
| 4,272,485 | 6/1981 | Lübbers | 422/68 |
| 4,321,057 | 3/1982 | Buckles | 422/58 |
| 4,351,709 | 9/1982 | Goetz | 204/180 R |
| 4,375,334 | 3/1983 | Gerber | 356/338 |
| 4,447,546 | 5/1984 | Hirschfeld | 436/527 |
| 4,470,697 | 9/1984 | Chraplyuy | 356/73 |
| 4,507,556 | 3/1985 | Brenholdt | 162/263 |
| 4,509,522 | 4/1985 | Manuccia et al. | 128/634 |
| 4,513,087 | 4/1985 | Giuliani et al. | 436/96 |
| 4,558,014 | 12/1985 | Hirschfeld et al. | 436/527 |
| 4,560,248 | 12/1985 | Cramp et al. | 350/96.34 |
| 4,582,809 | 4/1986 | Block et al. | 436/527 |
| 4,595,833 | 6/1986 | Sting | 250/353 |
| 4,606,636 | 8/1986 | Monin et al. | 356/338 |
| 4,608,344 | 8/1986 | Carter et al. | 436/34 |
| 4,656,331 | 4/1987 | Lillquist et al. | 219/121.47 |
| 4,679,939 | 7/1987 | Lurry et al. | 356/336 |
| 4,720,160 | 1/1988 | Hicks | 350/96.29 |
| 4,799,799 | 1/1989 | Sapko et al. | 356/446 |
| 4,806,289 | 2/1989 | Laursen | 350/96.34 |
| 4,818,710 | 4/1989 | Sutherland et al. | 422/82.07 |
| 4,893,894 | 1/1990 | Caimi | 350/96.29 |

FOREIGN PATENT DOCUMENTS 2508637 9/1976 Fed. Rep. of Germany .

OTHER PUBLICATIONS

Chemical Abstracts, vol. 97, 1982, 97:42973c, Infrared-Transmitting Fibers.
Chabay, Optical Waveguides, Analytical Chemistry, vol. 54, No. 9, Aug. 1982, pp. 1071-1080.
McCreery, Fiber Optic Probe for Remote Raman Spectrometry, vol. 55, No. 1, Jan. 1983, pp. 146-148.
The Condensed Chemical Dictionary, p. 297.

*Primary Examiner*—Richard V. Fisher
*Assistant Examiner*—John J. Bruckner
*Attorney, Agent, or Firm*—Michael J. Striker

[57] ABSTRACT

An arrangement for optical measuring concentration of substances has a measuring space which is composed of a material selectively permeable for particles to be measured, acting back on the particles and transparent for a measuring radiation, and a measuring space is arranged in working connection with the object to be measured and the measuring radiation passes through the measuring space. The measuring space has a layer that is a water-insoluble solvent or made of poly(ethylene terephthalate) or polytetrafluoroethylene. The layer excludes a reaction from the particles to be measured.

34 Claims, 4 Drawing Sheets

ARRANGEMENT FOR OPTICAL MEASURING OF CONCENTRATION OF SUBSTANCES

CROSS-REFERENCE TO RELATED APPLICATIONS

This application is a continuation-in-part of application Ser. No. 889,810 filed on July 24, 1986 now abandoned, which in turn is a continuation of application Ser. No. 679,018 filed on Dec. 6, 1984, now abandoned.

BACKGROUND OF THE INVENTION

The present invention relates to an arrangement for optical measuring of concentration of substances.

In biological objects of measurement, frequently concentration of fractions of particles must be determined and the determination is predominantly performed in aqueous solutions. In known methods, the distorting influence of particles which are not interesting for measurement or the distorting influence of water upon the particles to be measured is very high. In optical measurements frequently the measuring radiation is distorted so that quantitive measurements are questionable. While the particles which are optically measurable by luminescent or absorption indicators can be measured, for example in accordance with the DE-PS 2,508,637, by optodes or optical indicators containing indicator space, the optical measurement of infrared active particles or particles for which no indicators are available is problematic because of the above-mentioned circumstances.

SUMMARY OF THE INVENTION

Accordingly, it is an object of the present invention to provide an arrangement for optical measuring concentration of substances, which improves optical measurements of concentration of particles which are not measurable by optodes.

In keeping with these objects and with others which will become apparent hereinafter, one feature of the present invention resides, briefly stated, in an arrangement for optical measuring concentration of substances in which a measuring space is provided of a material which is selectively permeable for particles to be measured and transparent for a measuring radiation, and which is in operative connection with an object to be measured and through which the measuring radiation is transmitted.

When the arrangement is designed in accordance with the present invention it possesses the advantage that, on the one hand, because of the selectivity of the measuring space for the diffusing particles to be measured a separation of other distorting particles which are not to be measured is possible.

A further advantage is that the absorption curve for the radiation can be displaced in the cases in which the molecules which form the measuring space act back on the particles to be measured, which acts for displacement of the absorption. Thereby an additional possibility is obtained for determination of the wavelengths of an irradiator, an absorption region and a receiver relative to one another or the working region can be displaced out of the distorting band lying in the measuring region.

Moreover, with the utilization of substances for the measuring space which have a bond or a higher solubility coefficient for the particles to be measured, their concentration relative to the measuring space is increased and thereby the signal-noise ratio for the measuring radiation is improved.

The substances used as the measuring space must be transparent for the measuring radiation. Since such a transparency for example with silicons, PVC, polystyrene, polypropylene and the like is possible also for the infrared-measuring radiation, it is also possible to optically measure substances susceptible to diffusion without specific indicators but with impressed infrared activity or with Raman activity. The narcosis gas halothan is an example of this.

The arrangements in accordance with the present invention are suitable not only for simple transmission, but also can be used as light conductors or parts of light conductors. It is advantageous, when, for example a light conductor for the transportation of the measuring radiation is provided which is coated at its lateral surfaces with a measuring space.

For enabling performance of a light conduction in a light conductor, the transported light must extend at the lateral surfaces of the light conductor within the limiting angle of the total reflection. The light is then reflected by the limiting surface, and from physical grounds is not reflected ideally but extends through a short path substantially on the order of a wavelength, in the outer space. When a measuring space is arranged in accordance with the present invention, the measuring radiation penetrates through this measuring space. The effective thickness of the measuring is determined by the measuring radiation and its irradiation angle, or in other words, physically.

Since the measuring radiation from physical grounds cannot penetrate deeper in the measuring space, means for optical uncoupling of the measuring radiation from an object of measurement is no longer necessary. The measuring space has a thickness of several wavelengths.

If the solubility of the measuring space or the absorption for the type of particles to be measured is increased relative to the object to be measured by respective selection of the substance of which it is composed, then an increased concentration in the measuring space for these particles takes place and the signal/noise ratio of the measurements is thereby improved.

When several parameters or types of particles are measured a fielding of the measuring space is provided, and the indicator fields are formed particle-selective.

If the membrane is formed hydrophobous, then for example the particles to be measured which diffuse in the indicator space are separated from water. Thereby, it is for example possible to measure $CO_2$ concentration or concentration of narcosis gas (halothan) in blood or other aqueous solutions with the aid of infrared radiation. Conventionally this is not possible since the water has a very high infrared absorption by the so-called "water bands" which does not provide for infra-red measurements in transmitted light or reflection.

Materials for such light conductors associated with the measuring space can be for example thalliumbromide-iodide (KRS5), ZnSe, ZnS, Si, Ge, or, where it is technically possible, chrystalline heteropolar salt, such as CaF or KBr or NaCl.

The use of infra-red radiation for ATR measurement requires a much greater precision of the surface of the light conductor than is necessary for mere measurements of any other mode, because the aplanity of the surface must be below the magnitude of a wavelength. Furthermore, for ATR measurements the infra-red radiation must be carefully colimated (made parallel) and fed into the light conductor near the correct angle of total reflection. If the colimation is not done, no measurable ATR is achieved.

Further layers which coat the measuring space and serve as locks for water vapor can be composed for example of tetrafluoroethylene or mylar TM, poly(ethylene terephthalate). They also can be layers of water-insoluble solvents, such as for example, dioctylphthlate.

These means can be either self-adhesive or can be immobilized by porous meshwork, for example TEFLON TM, (polytetrafluoroethylene) fleece (milliporous filter) or the like.

It is also possible to use active polymer foils such as for example carrier-doped. Thereby an improved selectivity for the particles to be measured is obtained.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIGS. 10a and 10b illustrate different particle measurement embodiments.

DESCRIPTION OF THE PREFERRED EMBODIMENTS

Figure 1:
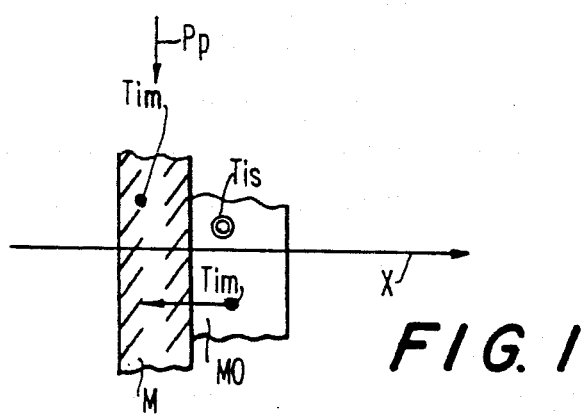
FIG. 1 is a view showing an arrangement for optical measuring concentration of substances in accordance with a first embodiment of the invention.
Figure 1A:
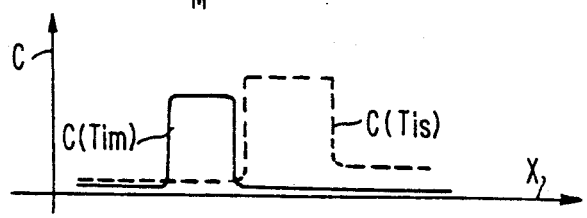
FIG. 1a is a diagram showing the concentrations of the substances.

As can be seen from FIG. 1, the measuring radiation $P_p$ passes through a measuring space M which is in working connection with an object to be measured MO. The particles fraction $T_{im}$ diffuses into the measuring space M and is located, when the solubility a for the particles $T_{im}$ in the measuring space M is higher than in the object to be measured MO, in increased concentration $C(T_{im})$ in accordance with FIG. 1a in the measuring space M. On the other hand, the particles $T_{is}$ which cannot diffuse into the measuring space M, such as for example, water, in the case of use of lipophilous measuring chamber, are spaced from the measuring space M, and thereby excluded from the measurement.

The concentration increase in the measuring chamber M can amount, depending upon the absorption and solubility, to three orders.

Figure 2:
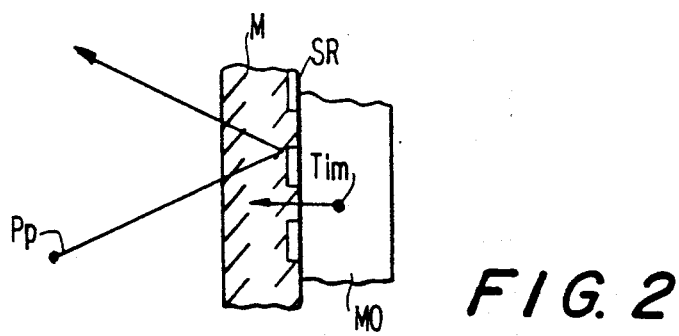
FIG. 2 is a view showing the inventive arrangement in accordance with a second embodiment.

When the provisions for measurement in a transmitted light, for transparent objects to be measured MO, are not available, measurements can be performed in a reflection in accordance with FIG. 2. In this case, the measuring space M can be closed after the object to be measured MO, with a partial reflection layer SR.

Figure 3:
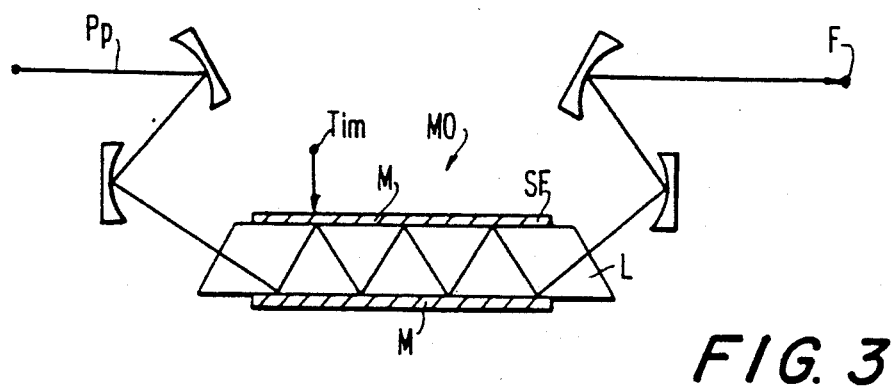
FIG. 3 is a view showing the inventive arrangement in accordance with a third embodiment.

When the measurements must be performed in very thin layers, the measuring chamber M in accordance with FIG. 3 can form a lateral surface SF of a light conductor L. Since the measuring radiation $P_p$ in the light conductor L extends under the limiting angle of the total reflection, during reflection a short path inside the measuring chamber M is covered over which an interference of the particles with this radiation can take place. A photoreceiver F receives this radiation.

Figure 4:
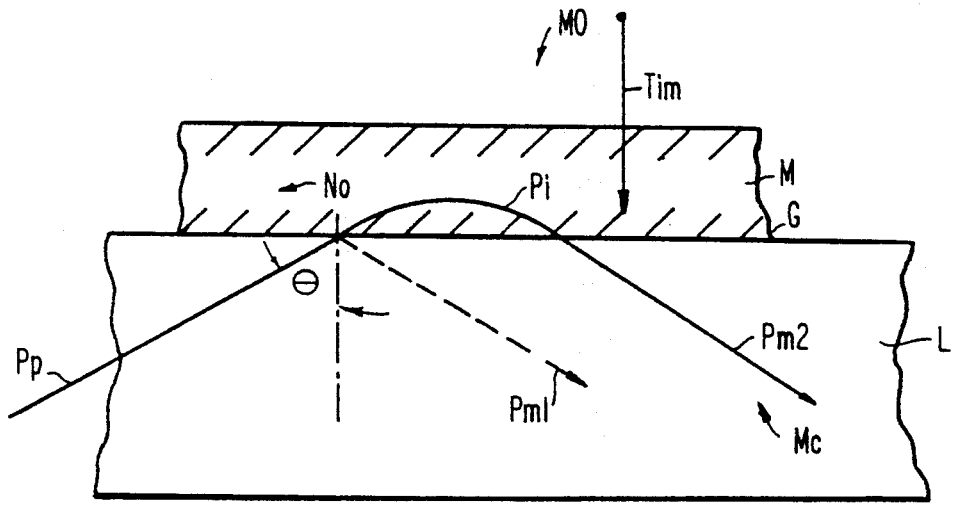
FIG. 4 is a view showing a part of the inventive arrangement in a section.

In FIG. 4 a beam of the measuring radiation $P_p$ reaches from the light conductor L with the refraction index $N_c$ a phase border G to the measuring space M with a refraction index $N_o$ which is lower than the abovementioned refraction index $N_c$. The beam $P_p$ is not reflected at the phase border G in an ideal manner as $P_{m1}$, but covers a path $P_i$ in the outer medium of the measuring space M. The amplitude is obtained in accordance with the following equation:

$$E = E_o e^{-Z/dp}$$

with $$dp = \frac{\lambda}{N_o^2 (\sin^2\theta - [N_o/N_c]^2)^{\frac{1}{2}}}$$

from the wave front of the beam $P_p$ a beam $P_{m2}$ is produced.

Figure 5:
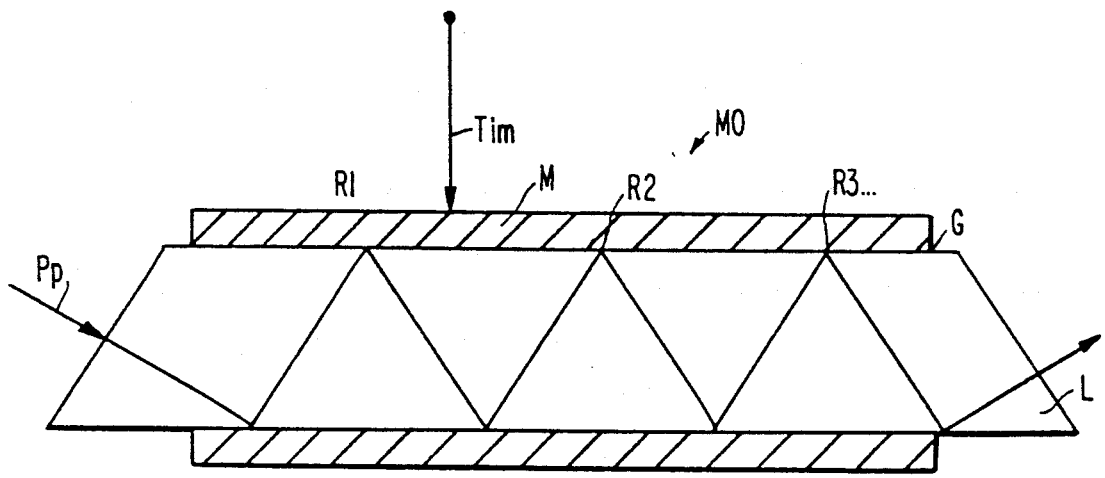
FIG. 5 is a view showing a light conductor in a section.

In a measuring arrangement in accordance with FIG. 5 the measuring radiation $P_p$ passes through a larger path in the light conductor L. Here the fact of the border surface absorption in the measuring space M is repeated many times as R1, R2, ..., so that the changes of the measuring radiation $P_p$ connected with the concentration are reinforced.

When the measuring chamber M is composed of a material with absorption or with high solubility coefficient a for a predetermined type of particle $T_{1m}$ then the concentration of $T_{im}$ in the measuring chamber M relative to the object to be measured MO increases. Thereby the concentration in the measuring space M can be increased by several orders.

When the measuring space M is formed hydrophobous, a separation of the outer space in a water-free measuring space M and the object to be measured MO takes place in the event of aqueous solution as an object to be measured. On the other hand, diffusion-susceptible substances diffuse into the measuring space M until they reach diffusion equilibrium with the object to be measured. The diffused substance which is thereby separated from distorting substances can now be optically analyzed from inside or in other words from the light conductor.

Because of the back damming of the water, the probe can be analyzed for example also with the infrared light, since the strong infrared absorption is effected by the water bands.

On the other hand, the transmission depth is adequately great because of the great wavelengths, so that for many measuring problems there are sufficient optical wavelengths in the measuring space. This is of an especial advantage, since now the whole infrared analytic technique for measuring spaces can be used and also Raman-active substances can be examined.

Figure 6:
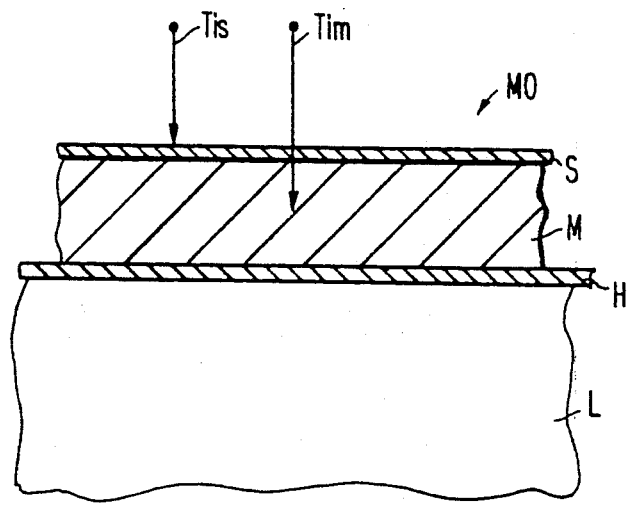
FIG. 6 is a view showing a multiple-layer arrangement in accordance with the invention.

The residues of water vapor can also be held far from the measuring space, when the measuring space is sealed in accordance with FIG. 6 with a further layer S, for example tetrafluoroethylene or mylar. Such layers are little permeable namely for water vapor ($T_{is}$), whereas for the particles to be measured $T_{im}$, oxygen, narcosis gas (halothan) or $CO_2$ they are well permeable so that these types of particles are concentrated especially well in the measuring space M and thereby can be well measured.

The layers can be connected by an adhesive agent H with the light conductor L.

Especially during the measurement in infrared region, the thermostatization of the measuring arrangement is advantageous since thereby the background radiation of the arrangement can be held constant.

Figure 7:
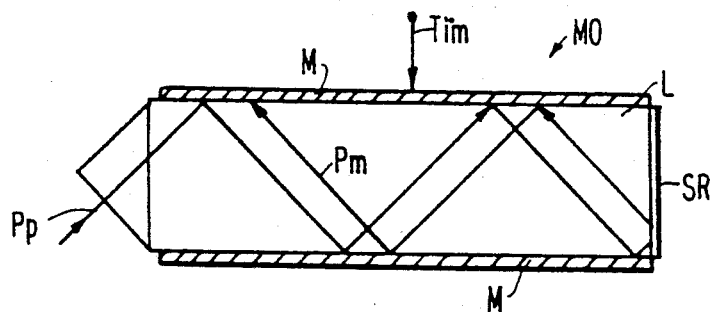
FIG. 7 is a view showing a light conductor used as a dip stick.

The light conductor in accordance with FIG. 7 is formed as a dip stick.

Figure 8:
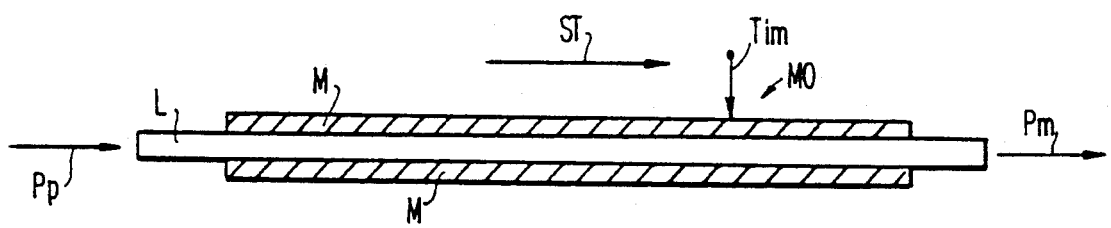
FIG. 8 is a view showing an elongated light conductor.

For measuring flowing liquids, the total reflection in the measuring space M can take place in accordance with FIG. 8 over long paths of the light conductor L, so that a more elongated thinner light conductor L can be used which distort less the stream ST.

Figure 9:
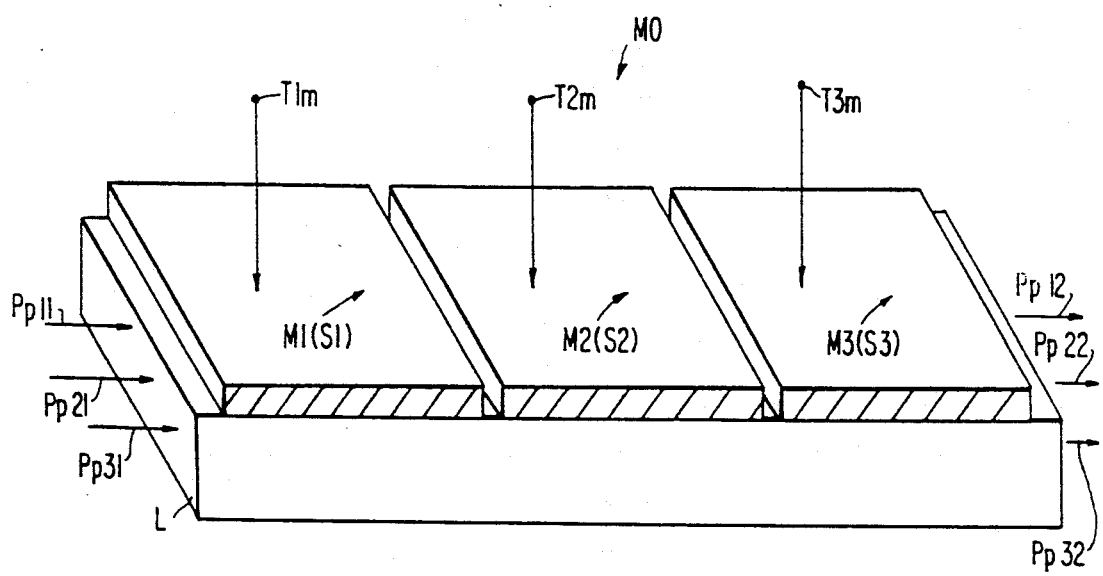
FIG. 9 is a view showing a fielded arrangement.

When simultaneously several types of particles $T_{im}$, $T_{2m}$, $T_{3m}$ ... are measured by testing light radiations $P_{p11}$, $P_{p21}$ ..., the measuring spaces $M_1(S1)$ $M_2(S2)$, ..., in accordance with FIG. 9 are fielded and formed of or covered with different substances which are selective to the particles $S_1$, $S_2$, ... With the particle-selective substances only predetermined type of particles $T_{im}$ can be transmitted by diffusion into the measuring space $M_i(Si)$. They are measured by determination of the change of the associated radiations $P_{p11}$, $P_{21}$, ... in accordance with $P_{p21}$, $P_{p22}$ ....

If one testing light radiation $P_{1i}$ is independent of the measuring process, it can be used as a reference radiation in that the other measured intensities can be related to this radiation intensity. Thereby the intensity deviation caused by the apparatus can be eliminated by computations in known manner.

Figure 10A:
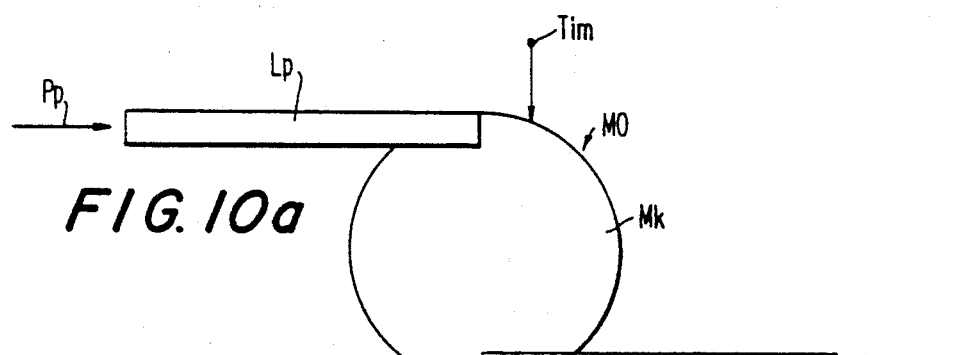
FIGS. 10a and 10b are views showing a cylindrical measuring chamber with light conductors extending in different directions respectively.
Figure 10B:
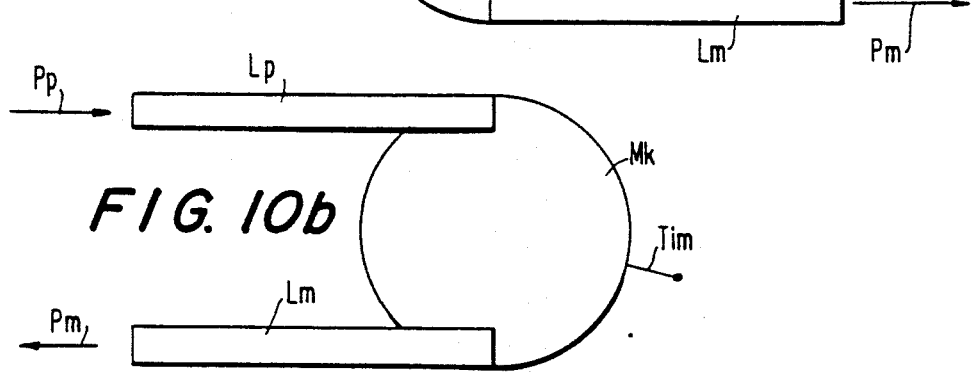

If furthermore, the measuring arrangement MK must occupy only a small space, it can be formed in accordance with FIGS. 10a and 10b cylindrically or spherically and arranged on the measuring space. The testing light $P_p$ passes respectively tangential through a light conductor $L_p$ into the measuring space $M_k$, and the measuring radiation $P_m$ exists tangentially through a light conductor $L_m$. Arrangements in accordance with FIG. 10a are suitable for the measurement of Raman-active substances, arrangements in accordance with FIG. 10b are suitable for measurement of absorption substances.

The embodiment of FIG. 10a is used for Raman-active particles. In this case the exciting IR-radiation is entering the conductor LP. The curvature of the cylinder must have the appropriate angle (for having total reflection). Since the exciting radiation cannot leave the cylinder (because of the "wrong-direction" of conductor LM), the exciting radiation is running the cylinder until completely absorbed by the Raman active particles which have gathered in the film coating of the chamber MK. The Raman radiation, which is emitted by every of the particles excited by the exciting IR radiation is running undirected into the chamber MK and is eventually leaving the cylinder by conductor LM (and LP). Thus, in the conductor LM a very good separation of Raman radiation and exciting radiation is found. (Low intensity IR radiation, relatively high intensity of Raman radiation, this Raman radiation leaving MK through LM is emerging from the left part of side of the chamber MK).

In the embodiment of FIG. 10b, absorbing particles, for instance $CO_2$ particles, which have gathered in the film coating of the chamber MK are attenuating the IR light. This attenuated light is leaving via light conductor LM (which is positioned in the "right direction" for the exciting IR radiation). The attenuation takes place at the left side of the chamber MK.

When with particle measurements only small particle quantities are available, it is advantageous to maintain the solubility a of the measuring space small and also to get rid of sensitivity increase so as not to provoke reduction of particles to be measured which can distort the measuring results.

The material of said measuring space can have absorption points for a material to be measured. The measuring space can be composed of a polymer selected from the group consisting of organic and inorganic polymers. The light conductor can be formed as a dip stick covered with a mirror. The measuring space can be thermostatisized. The measuring space can be composed of a substance arranged in a substance forming a porous meshwork. Finally, the measuring space can have a carrier selective to the particles to be measured.

It will be understood that each of the elements described above, or two or more together, may also find a useful application in other types of constructions differing from the types described above.

While the invention has been illustrated and described as embodied in an arrangement for optical measuring concentration of substances, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. An arrangement for optical measuring concentration of substances, comprising means defining a measuring space composed of a material which is permeable for particles to be measured, said measuring space being transparent for a measuring radiation, said measuring space being water repellant and free from any indicator, said measuring space having a light conductor which has a refractive index greater than that of the measuring space and is not permeable for particles to be measured and that the measuring radiation passes through said measuring space by attenuated total reflection; means for producing a testing light, which is an infrared radiation; and a layer arranged to be in connection with said measuring space, said layer excluding a reaction from the particles to be measured, said layer being composed of a water-insoluble solvent.

2. An arrangement as defined in claim 1, wherein the measuring space material is selected measured.

3. An arrangement as defined in claim 2, wherein said measuring space materials are selected from the group consisting of silicon, polyvinylchloride, polystyrene, and polypropylene.

4. An arrangement as defined in claim 1, wherein said measuring space contains measuring fields for the particles to be measured.

5. An arrangement as defined in claim 4; and further comprising a radiation source providing the measuring radiation and formed to produce different wavelengths.

6. An arrangement as defined in claim 1, wherein said light conductor has a surface provided with said measuring space.

7. An arrangement as defined in claim 6, wherein said light conductor is a dip stick covered with a mirror.

8. An arrangement as defined in claim 6, wherein said light conductor is an elongated light conductor.

9. An arrangement as defined in claim 1, wherein said measuring space is cylindrical, said light conductor being arranged tangentially to said measuring space for producing the measuring radiation through the light conductor to the measuring space.

10. An arrangement as defined in claim 1, wherein said measuring space material has absorption points for absorption of the particles to be measured.

11. An arrangement as defined in claim 1, wherein said layer is connected with said measuring space by an adhesive agent.

12. An arrangement as defined in claim 1, wherein said measuring space is spherical, said light conductor being arranged tangentially relative to said spherical measuring space for passing the measuring radiation through the light conductor to the measuring space.

13. An arrangement as defined in claim 1, wherein said measuring space material displaces a wavelength of absorption of the particles to be measured.

14. An arrangement as defined in claim 1, wherein said measuring space contains a substance forming a porous meshwork.

15. An arrangement as defined in claim 1, wherein said measuring space has a carrier for the particles to be measured.

16. An arrangement as defined in claim 1, wherein said light conductor is composed of a material selected from the group consisting of thalliumbromide-iodide or calcium fluoride.

17. An arrangement as defined in claim 1, wherein said layer is composed of dioctylphtalate.

18. An arrangement as defined in claim 17, wherein said light conductor is connected with said measuring space by an adhesive agent.

19. An arrangement as defined in claim 17, wherein said light conductor is composed of a material selected from the group consisting of thalliumbromide-iodide or calciumfluoride.

20. An arrangement for optical measuring concentration of substances, comprising means defining a measuring space composed of a material which is permeable for particles to be measured, said measuring space being transparent for a measuring radiation, said measuring space being water repellant and free from any indicator, said measuring space having a light conductor which has a refractive index greater than that of the measuring space and is not permeable for particles to be measured and that the measuring radiation passes through said measuring space by attenuated total reflection; means for producing a testing light, which is an infrared radiation; and a layer arranged to be in connection with said measuring space, said layer excluding a reaction from the particles to be measured, said layer being composed of a material selected from the group consisting of tetrafluoroethylene and poly(ethylene terephthalate).

21. An arrangement as defined in claim 20, wherein the said measuring space contains a material which is selected so that it has a high solubility coefficient for the particles to be measured.

22. An arrangement as defined in claim 21, wherein said measuring space materials are selected from the group consisting of silicon, polyvinylchloride, polystyrene and polypropylene.

23. An arrangement as defined in claim 20, wherein said measuring space has fielding and measuring fields are formed selectively for the particles to be measured.

24. An arrangement as defined in claim 23; and further comprising a radiation source providing the measuring radiation and formed to produce different wavelengths.

25. An arrangement as defined in claim 24, wherein said radiation source is formed so that one of said wavelengths provided by said radiation source has a reference wavelength.

26. An arrangement as defined in claim 20, wherein said light conductor has a surface provided with said measuring space.

27. An arrangement as defined in claim 26, wherein said light conductor is a dip stick covered with a mirror.

28. An arrangement as defined in claim 26, wherein said light conductor is an elongated light conductor.

29. An arrangement as defined in claim 20, wherein said measuring space is cylindrical, said light conductor being arranged tangentially to said measuring space for passing the measuring radiation through the light conductor to the measuring space.

30. An arrangement as defined in claim 20, wherein said measuring space is spherical, said light conductor being arranged tangentially relative to said spherical measuring space for passing the measuring radiation through the light conductor to the measuring space.

31. An arrangement as defined in claim 20, wherein said measuring space material has absorption points for absorption of the particles to be measured.

32. An arrangement as defined in claim 20, wherein said measuring space material displaces a wavelength of absorption of the particles to be measured.

33. An arrangement as defined in claim 20, wherein said measuring space contains a substance forming a porous meshwork.

34. An arrangement as defined in claim 20, wherein said measuring space has a carrier for the particles to be measured.

* * * * *